(12) United States Patent
Walt et al.

(10) Patent No.: US 7,274,844 B2
(45) Date of Patent: Sep. 25, 2007

(54) LIGHT-EMITTING TEXTILE STRUCTURE, IN PARTICULAR FOR MEDICAL PURPOSES, AND USE THEREOF

(75) Inventors: Heinrich Walt, Zollikerberg (CH); Bärbel Selm, Berg (DE); Thomas Wessel, Männedorf (DE)

(73) Assignee: University of Zurich EMPA (CH)

( * ) Notice: Subject to any disclaimer, the term of this patent is extended or adjusted under 35 U.S.C. 154(b) by 132 days.

(21) Appl. No.: 11/126,843

(22) Filed: May 11, 2005

(65) Prior Publication Data

US 2006/0257095 A1 Nov. 16, 2006

(51) Int. Cl.
*G02B 6/26* (2006.01)
*F21V 21/08* (2006.01)

(52) U.S. Cl. .................. 385/38; 385/147; 362/103
(58) Field of Classification Search .............. None
See application file for complete search history.

(56) References Cited

U.S. PATENT DOCUMENTS 4,234,907 A    11/1980  Daniel
4,727,603 A    3/1988   Howard
6,709,142 B2*  3/2004   Gyori ..................... 362/554
6,970,623 B2*  11/2005  Vernooy .................. 385/43

FOREIGN PATENT DOCUMENTS

| EP | 0 359 450 A2 | 3/1990 |
| GB | 2107571 A * | 5/1983 |
| GB | 2 305 848 A | 4/1997 |

* cited by examiner

*Primary Examiner*—Kevin S Wood
*Assistant Examiner*—Jerry T Rahll
(74) *Attorney, Agent, or Firm*—Bolesh J. Skutnik; BJ Associates

(57) ABSTRACT

A light-emitting textile structure, which in particular is useful for medical purposes, comprises a flat support (2) and a plurality of light-emitting elements (4) fixed thereto. Each light-emitting element comprises a light-supplying optical fiber (6), to each optical fiber (6) there being associated exactly one light-emitting element (4), which comprises at least one output zone formed by a local curvature of the optical fiber. The local curvature is selected in such a way that a lateral exit of light from the optical fiber occurs due to the absence of total reflection.

13 Claims, 5 Drawing Sheets

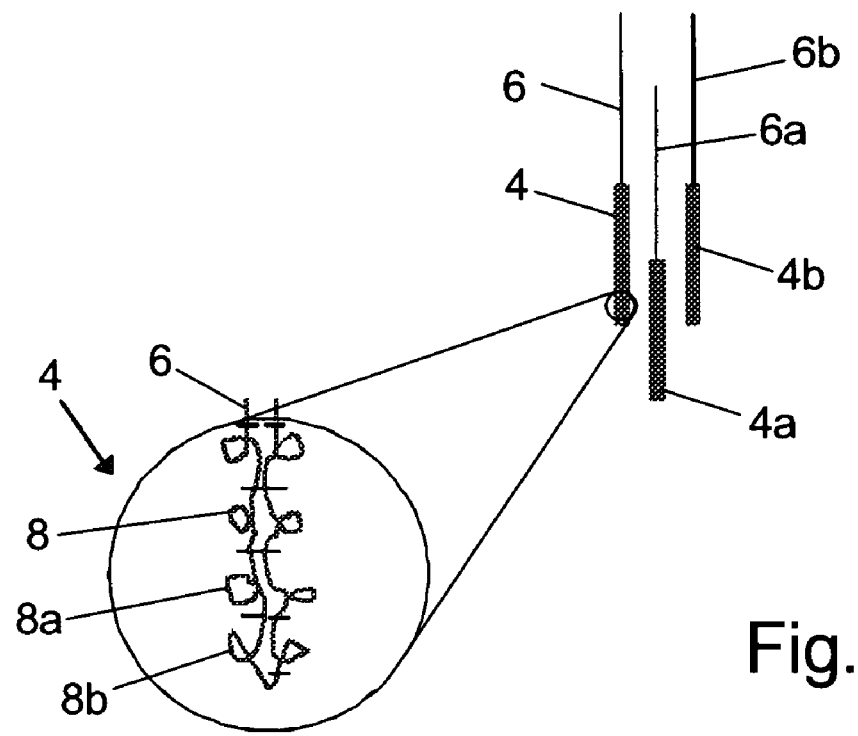
Fig. 2
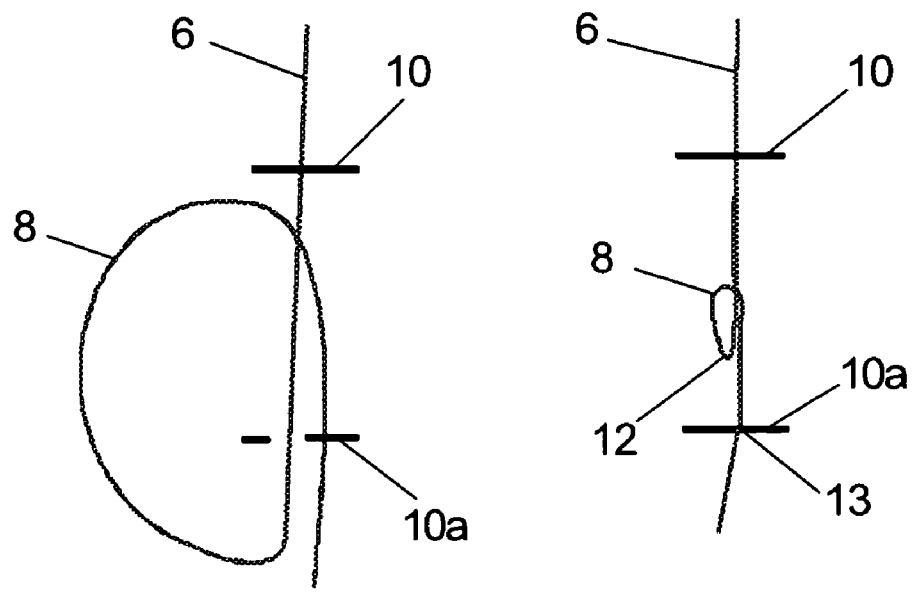
Fig. 3
Fig. 4

LIGHT-EMITTING TEXTILE STRUCTURE, IN PARTICULAR FOR MEDICAL PURPOSES, AND USE THEREOF

FIELD OF THE INVENTION

The invention relates to a light-emitting textile structure according to the preamble of claim 1 and to a use thereof.

PRIOR ART

A related textile structure is disclosed in EP 0 359 450 A2. The textile structure described therein is designed as a light-emitting plate having at one side thereof a plurality of woven optical fibers provided with bends at discrete locations along the length of the fibers. These bends have the effect that light guided within the fibers is laterally emitted from the optical fibers at the bend zones due to the absence of total reflection. As possible uses of the light-emitting plate, there are described, amongst others, phototherapeutic treatments, for example the phototherapy of jaundice in newborns.

The known light-emitting textile structure is made in the way of a woven fabric in which the light guiding fibers are arranged as warp threads and the bends acting as light-emitting elements are situated at the intersections of the warp threads with transversally oriented weft threads. Accordingly, to each light guiding fiber there is associated a plurality of light-emitting elements that are arranged adjacent to each other in a pearl string fashion. An important disadvantage of this type of arrangement is caused by the fact that the light emission intensity of the individual light-emitting elements decreases along the fiber. If, for example, a certain fraction of the light present in the fiber at any given light-emitting element is emitted laterally, then the light emission intensity along the fiber will decrease in a substantially exponential fashion. In order to achieve an approximately homogeneous distribution of light emission across the entire structure, care has to be taken that the fraction of light emerging from individual light-emitting elements gradually increases along the light guiding fiber. Alternatively, it can be attempted to gradually reduce the distance between light-emitting elements along the light guiding fiber in order to compensate for the decreasing intensity per light-emitting element with a higher density of light-emitting elements. However, this is a demanding task, which is particularly difficult to realize with a woven-type textile structure, which as a rule is built up periodically. For all these reasons, it is hardly possible to achieve a homogeneous distribution of light emission with the light-emitting textile structure disclosed in EP 0 359 450 A2. This, however, is against the requirements of many applications, particularly many medical applications that require that the illumination of an area to be irradiated with light be as uniform as possible.

The arrangement of light-emitting elements in a pearl string fashion according to EP 0 359 450 A2 is also not useful for applications in which an illumination with a predefined inhomogeneity is specifically required. Again, the sequential arrangement of light-emitting elements turns out to be a substantial limitation, as the intensity distribution along a chain of light-emitting elements is substantially predefined, i.e. it is merely possible to arbitrarily vary the intensity in transverse direction with respect to the optical fibers by specifically providing the various fibers with light of differing intensity. In longitudinal direction, however, no variation of intensity is possible for a given arrangement of the woven fabric.

A further light-emitting structure is disclosed in GB 2 305 848 A, which contains optical fibers in textile structures of various type, i.e. apart from woven fabrics there are also mentioned knitted and plaited structures. Importantly, the lateral exit of light is not achieved necessarily by wavy optical fibers. Rather than that, still before being worked to form the structure, the fibers are provided with local damages of their lateral surface which act as light output zones of the fiber. As examples for such damages, there are mentioned notches, grooves, indentations and further irregularities of the surface. The problem that intensity decreases along each optical fiber is not mentioned in GB 2 305 848 A, however.

U.S. Pat. No. 4,234,907 discloses a light-emitting woven fabric that has optical fibers as warp threads and other fibers as weft threads. Again, a lateral emission of light out of the optical fibers is achieved by local damages, particularly scratches. In order to compensate for the decrease of the intensity along individual fibers, the damage zones are arranged increasingly closer to each other with increasing distance from the light source. Although this solution allows for an approximately homogeneous distribution of light emission across the entire light-emitting woven fabric, there is no possibility to generate an inhomogeneous distribution of a given shape in warp direction once the woven fabric is finished. For example, it is not possible to generate a stripe with brighter intensity in any arbitrary direction, although this would be desirable for many applications.

U.S. Pat. No. 4,727,603 discloses a garment with light guiding fibers stitched onto it. Again, these are optical fibers whose surface is provided with a plurality of small damages. It is intended to provide the garment with light-emitting ornaments, which, for example, represent flower or leave motives. Each one of these motives is formed from a plurality of line-type light-emitting fibers. The problem of intensity decrease along the fibers is not mentioned; however, the provision of a homogeneously fluorescing textile structure is just not the aim of U.S. Pat. No. 4,727,603. On the other hand, the non-homogeneous distribution of light emission is predetermined by means of the stitching pattern, and a subsequent modification thereof is either not possible or is possible only to a limited amount.

AIMS AND SUMMARY OF THE INVENTION

An aim of the present invention is to provide an improved light-emitting textile structure that allows overcoming the disadvantages mentioned hereinabove. In particular, this textile structure shall be useful for general illumination purposes, but also for medical and veterinary applications.

The aim is achieved with the textile structure defined in claim 1. Said structure comprises a flat support and a plurality of light-emitting elements fixed thereto, each light-emitting element comprising a light-supplying optical fiber. Due to the fact that to each optical fiber there is associated exactly one light-emitting element, which therefore may be addressed individually, the light emission intensity of any given light-emitting element is individually controllable by inputting light of appropriate intensity into the associated fiber. In this way, the textile structure can be made to have either a highly homogeneous distribution or any arbitrary type of inhomogeneous distribution of light emission.

Furthermore, the light emission distribution can be changed without need for any changes of the textile structure simply by varying the intensity of the light that is coupled into the individual fibers. Any individual light-emitting element is formed by one or preferably by several output zones, each of which is formed by a local curvature of the optical fiber, the local curvature being selected in such a way that due to the absence of total reflection there is a lateral exit of light from the fiber, i.e. from its external surface. In this way the individual light-emitting elements can be designed in a very compact manner, thus permitting a large number of light-emitting elements per unit area and thus allowing for good control of the light emission distribution of the textile structure. Because the individual light-emitting elements are functional units that are independent of each other, a light-emitting textile structure with very high flexibility can be produced by means of an appropriately designed support. Therefore, the light-emitting textile structure of the present invention is not only useful for illumination of flat objects, but also for the illumination of structured objects. For example, in medical treatment it can be used like a conventional textile structure on the skin and for other internal and external organs of the body.

With appropriate manufacturing conditions, the light-emitting textile structure of the present invention can be produced very economically and is, therefore, also useful for once-only use, i.e. as a disposable item.

The most important applications of the textile structure of this invention are photodynamic diagnostics and photodynamic therapy of various malignant tumors (for example solid tumors like carcinomas and sarcomas) and their metastases as well as their precursors. Further application domains are pathological cell proliferations (e.g. endometriosis). Still further applications concern wound healing in various chronic diseases (e.g. diabetes or skin diseases), biostimulation as well as control of viral and bacterial infections, which can also be an advantage in dentistry. Furthermore, the textile structure of this invention can generally used for elimination of microorganisms on various surfaces.

A particular use of the textile structure is defined in claim 15. Thereby, at least one output zone of an optical fiber is used as light collector in order to lead light impinging onto the textile structure away through the optical fiber. For example, this allows determining—continuously or from time to time—the fluorescence intensity of an irradiated object, in particular of an irradiated tissue region. In this way, photodynamic diagnosis can be performed in situ, thus offering significant advantages in comparison with conventional methods.

Advantageous embodiments of the invention are defined in the dependent claims.

In principle, the light-emitting elements can be arranged on the support in various ways, with regular and irregular arrangements being possible. In the embodiment according to claim 2 the light-emitting elements form a pixel-like arrangement in the fashion of a regular grid. In this way, it is possible, on the one hand, to achieve a homogeneous light emission distribution by supplying each light-emitting element substantially with the same light intensity. On the other hand, the pixel-like arrangement is also suited for generating predefined inhomogeneous light emission distributions. In this context, it turns out to be advantageous if the light-emitting elements are distributed homogeneously on the support and each of the light-emitting elements is uniquely characterized by a row number and a column number. Therefore, a desired light emission distribution can be achieved by expressing it as a function of two coordinates, which substantially correspond to the above mentioned row numbers and column numbers, respectively; and subsequently feeding the optical fibers associated to individual light-emitting elements with light of an intensity that corresponds to the function values.

In principle, there are various possibilities for fixing the light-emitting elements to the support. Advantageously, the light-emitting elements are stitched to the support according to claim 3. In this way, it is possible to achieve a well-defined arrangement of the individual light-emitting elements at the intended positions on the support while nonetheless having a rather loose arrangement of the supplying optical fibers. The result is a light-emitting textile structure having great flexibility.

The individual optical fibers can be laid out substantially in a straight line, with only the region of the associated light-emitting element requiring one or several loops. According to claim 4, however, the individual optical fibers are arranged in U-shaped fashion with a light-emitting element lying proximally to the vertex. This has the advantage that to each light-emitting element there are associated two sides of the associated fiber, both of which may be used for supplying light to the light-emitting element. In particular, the two related sides can be gathered terminally to form a single light input zone.

In the embodiment according to claim 5 the output zone is formed by a loop of the optical fiber. The curvature of the loop shall be chosen in such a way that at least at certain locations of the loop a lateral exit of light is made possible by the absence of total reflection.

A further embodiment of the output zone is defined in claim 6, according to which the output zone is formed by a local damage or distortion of the optical fiber. The above-mentioned damage or distortion zones act as scattering centers for the light guided in the fiber, thus allowing for a lateral exit of light. In particular, in the stitched embodiment according to claim 2, the local damage or distortion zones can be generated by the action of the fixation stitches. This means that the output zones are only formed during the stitching process, which obviates the need for a demanding pretreatment of the optical fibers.

It is possible to form the individual optical fibers according to claims 5 and 6, i.e. to provide them with output zones that are loop-shaped type and are formed by local damages or distortions.

Advantageously, the material of the support is chosen according to the intended application. For example, according to claim 8 the support can be formed by a textile material or else by a foil. According to the embodiment defined in claim 9 the support can be removed before starting use of the textile structure. In particular, the textile structure including its support can first be placed at a desirable location, for example on the skin or within the body of a patient, and subsequently the support can be removed before starting light irradiation. Removability may optionally be realized by using a soluble material for the support.

The textile structure according to claim 10 has a light reflecting backside that allows an increased light emission in the opposite front direction. A particularly homogeneous light emission distribution can be achieved with the textile structure according to claim 11, which is provided at the front side thereof with an optically effective layer. In the present context, an optically effective layer may be any type of material sheet that exerts a predefined influence on the emission characteristics of the textile structure. In particular, said sheet may act as diffuser. Advantageously, the textile structure is provided both with a light-reflecting backside and with an optically effective layer arranged at the front side thereof.

The embodiment defined in claim 12 is designed for medical purposes, in particular for photodynamic therapy. The textile structure is coated with a photosensitive substance (a photosensitizer) or with a precursor thereof and is designed in the fashion of a patch. Therefore, with a one-time approach to the body area to be treated, it is possible to first deliver the photosensitizer or its precursor and to then perform the photodynamic treatment—optionally after waiting until a conversion of the precursor has occurred.

In the textile structure according to a further embodiment, the optical fibers are gathered terminally to form at least one fiber bundle. In this way, the textile structure can be attached to existing light sources in known ways. A further embodiment is defined in a further embodiment, according to which the textile structure is provided with light input means that allow controlling the light supply into individual optical fibers.

BRIEF DESCRIPTION OF THE DRAWINGS

Working examples of the invention are described more closely below with reference to the drawings, which show:

FIG. 2: three light-emitting elements of the textile structure of FIG. 1, in schematic representation, and a section of one of the light-emitting elements in enlarged representation;

FIG. 3: an optical fiber held in place with two fixation stitches, with a prearranged loop, in a schematic representation;

FIG. 4: the fiber of FIG. 3, with the loop pulled together;

DETAILED DESCRIPTION OF THE INVENTION

General Remarks

In the field of medicine, textiles are mainly used as patches or wound dressings, but also as implants, whereas until recently they were not used for light guiding functions.

For some time now, photosensitive substances (photosensitizers) are commercially available which specifically accumulate in pathological cells. Due to their photophysical and photochemical properties, photosensitizers accumulated in such cells and irradiated with non-ionizing electromagnetic radiation can be used for identification and localization of pathological cells by means of the fluorescence emitted therefrom (photodynamic diagnosis), and also for destruction of such cells by means of photochemical reactions (photodynamic therapy). In connection with these photosensitizers, light distributors providing a planar homogeneous irradiation are needed so as to allow for a specific treatment of certain skin regions, particularly of skin wrinkles and in structured hollow regions of the organs. Up to now, applications within the body relied on costly instruments such as balloon catheters, the use of which is limited by the inaccessibility of certain skin regions and by the inadequately controllable dosimetry. Actually, one mainly uses irradiation devices that comprise a fiber optical light supply, which allows to homogeneously illuminating a given area by of an expansion optic. While this type of the application leads to good results on smooth and primarily external skin areas, it is in most cases inadequate for structured surfaces.

EXAMPLES

Figure 1:
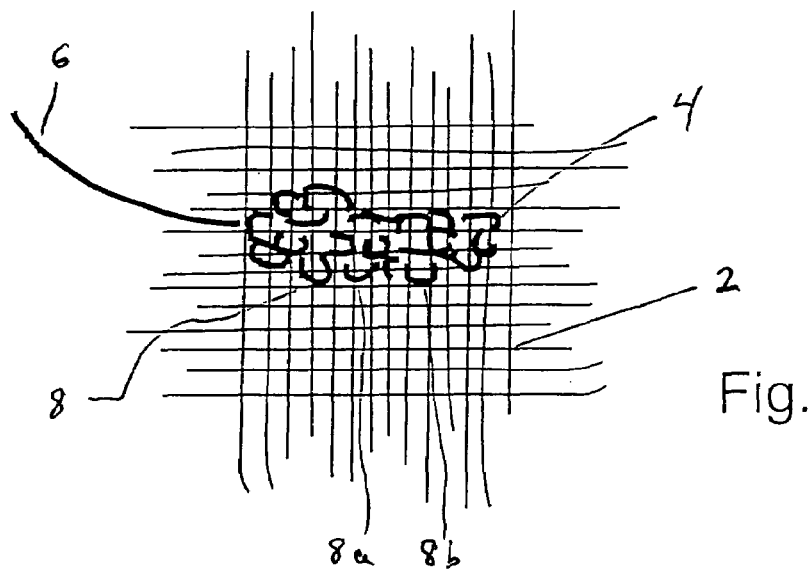
FIG. 1: a section of a light-emitting textile structure, in a schematic representation.

FIG. 1 shows a section of a light-emitting textile structure that comprises a flat support 2 onto which is affixed a light-emitting element 4 with a light-supplying optical fiber 6. The light-emitting element 4 comprises a number of loops 8, 8a, 8b, etc., the curvature of which is selected in such a way that a lateral exit of light from the optical fiber 6 occurs due to the absence of total reflection. Therefore, the above-mentioned loops act as output zones. It should be noted that the light-emitting element shown in FIG. 1 is formed from a single optical fiber, and for reasons of drawing only the parts of the fiber 6 that lie above the drawing plane are shown. The light-emitting elements can be attached to just one side or to both sides of support 2 depending on what type of application the textile structure is intended for.

In its entirety, the light-emitting textile structure comprises a plurality of light-emitting elements with associated optical fibers, with exactly one light-emitting element being associated to each optical fiber. This is shown schematically in FIG. 2, where three light-emitting elements 4, 4a, 4b are shown together with associated single optical fiber 6, 6a, 6b. The magnified section of FIG. 2 shows part of the light-emitting element 4 with a number of loops 8, 8a, 8b, etc. In this example, the light-emitting elements are fixed to a support not shown by means of fixation stitches 10.

The formation of local curvatures of the optical fiber as required for the function of the light-emitting elements is shown schematically in FIGS. 3 and 4. In this process, an optical fiber 6 is first laid out on a support (not shown here) so as to form a loop 8. Subsequently, the fiber is stitched on to the support by means of two fixation stitches 10, 10a in such a way that the loop region 8 lies between the two fixation stitches. Finally, the fiber is stretched in longitudinal direction L, so that the loop 8 is progressively pulled close. Upon pulling close, the curvature radius of the loop strongly decreases and, moreover, the fiber is twisted in the region of the loop. When the curvature radius at a site 12 of the loop falls below a critical value, the condition for total reflection of the light guided within the optical fiber is no longer fulfilled. Therefore, a lateral exit of light from the fiber occurs. The condition for total reflection depends on various factors such as wavelength of the light, refraction index etc., the relations of which are known in the art.

Local regions with strong curvature that may act as light exit zones are also generated either when applying the fixation stitches or by their effect thereafter. On the one hand, applying the fixation stitch can cause a damage of the side surface of the optical fiber. On the other hand, as indicated in FIG. 4, a local kink 13 can develop under pulling strain of the optical fiber 6 in the region of a fixation stitch 10*a*. Differently than shown in the example of FIG. 4, damages and distortions acting as output zones can be generated under the influence of fixation stitches also without loop formation.

Advantageously the individual optical fibers are arranged in a U-shaped fashion with the associated light-emitting element lying vertex-proximally as shown in the magnified section of FIG. 2. This has the advantage that to each light-emitting element there are associated two sides of the associated fiber, both of which can be used for light supply to the light-emitting element. However, it is also possible to arrange the light-emitting element at the end of the associated optical fiber, as shown in FIG. 1.

Figure 5:
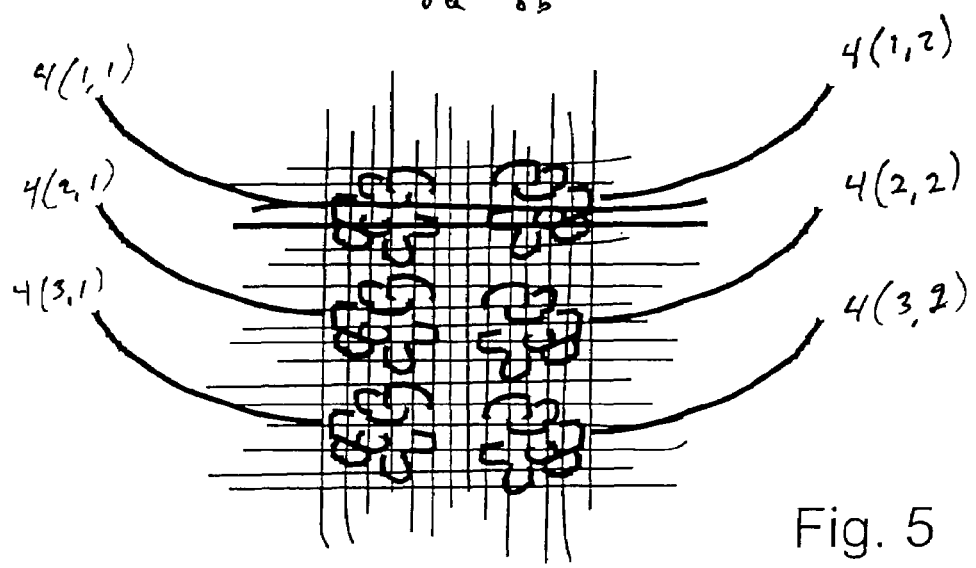
FIG. 5: a light-emitting textile structure with pixel-like arrangement of the light-emitting elements, in a schematic representation.
Figure 6:
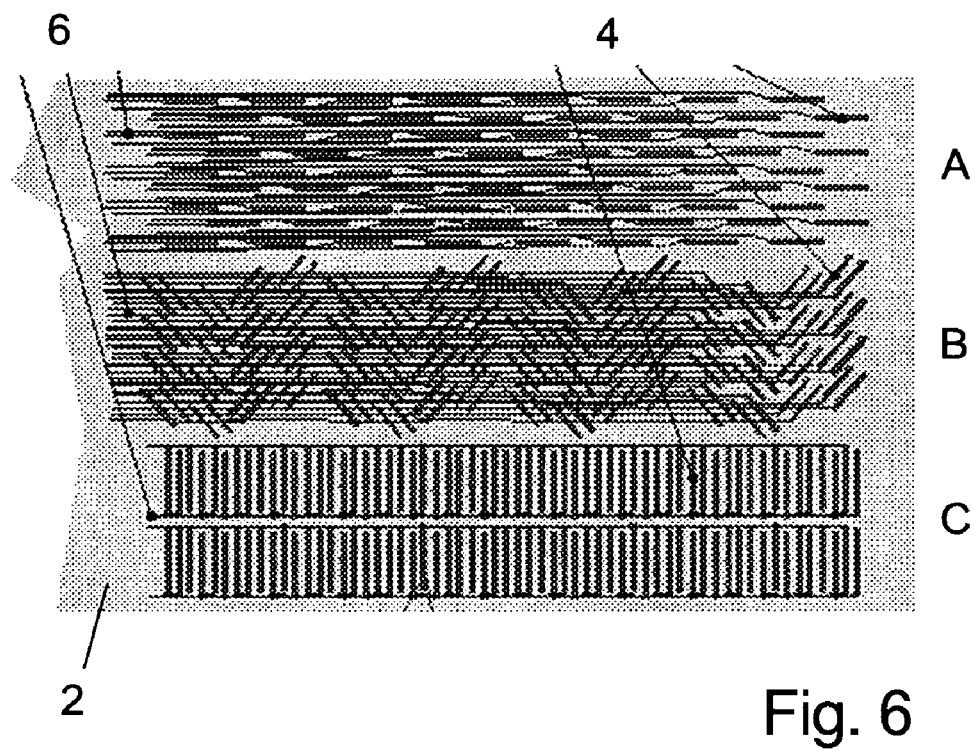
FIG. 6: a light-emitting structure with three different layout types of oblong light-emitting elements, in a schematic representation.

FIG. 5 represents a pixel-like arrangement of light-emitting elements exemplified by a section with six light-emitting elements 4 (j,k) characterized by a row index j=1, 2, 3 and a column index k=1, 2. Further possibilities of arrangement are represented in FIG. 6, which shows a textile structure having longitudinally formed light-emitting elements 4 with three different orientation modes A, B, C. It should be mentioned that the optical fibers and the light-emitting elements are in a unique relation to each other, i.e. to each optical fiber there is associated exactly one light-emitting element and vice versa. The fact that this is not readily seen in case of the orientation mode C in FIG. 6 is merely due to reasons of drawing.

Figure 7:
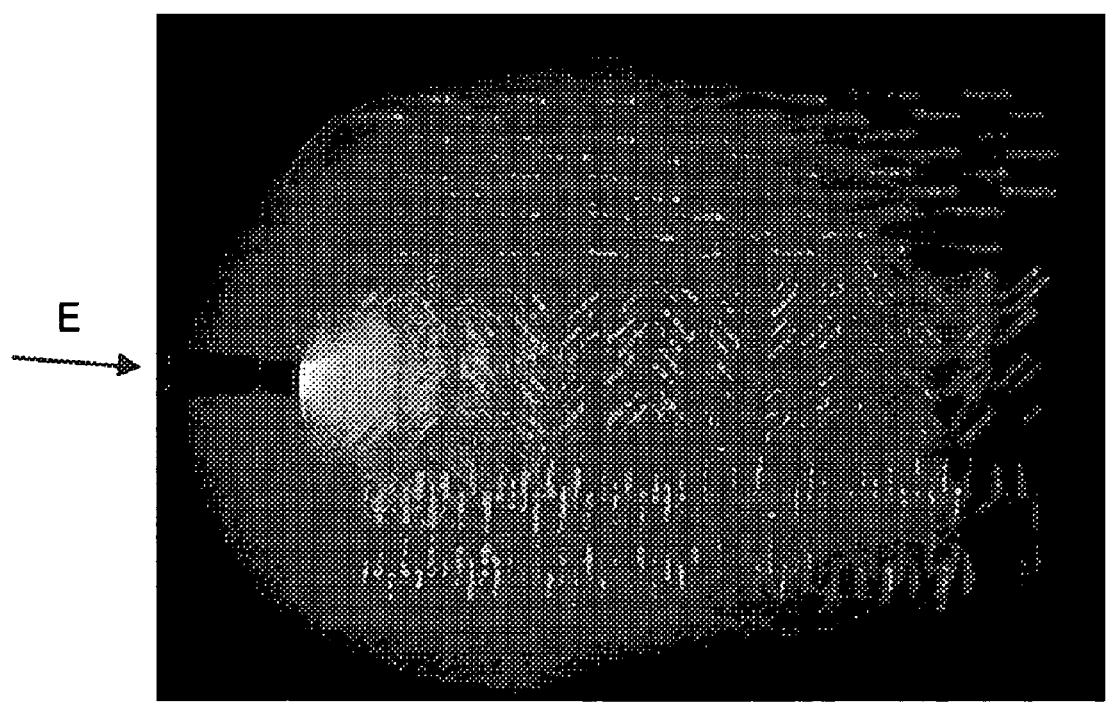
FIG. 7: the light-emitting textile structure of FIG. 6, in operating state, as a photographic reproduction.

FIG. 7 shows a photographic reproduction of a light-emitting textile structure according to FIG. 6 in operating state, i.e. with coupling in of red light into the optical fibers, but without any light scattering layer at the front side. The textile structure has a width of approximately 80 mm and a length of approximately 100 mm and is provided with approximately 300 light-emitting elements.

As a rule, these light waveguides consist of a light-conducting core that is provided with a cladding. Basically, light waveguides made of glass or synthetic material can be used as optical fibers. Particularly useful for medical use are optical fibers made of polymethylmethacrylate (PMMA), which are known from data transmission technology. Further useful fiber materials are polycarbonate (PC) and polystyrene (PS) or other amorphous synthetic materials such as polyamides (PA). For the optical fibers one can use monofilaments or multifilaments, which can be used as treated or untreated, coated or uncoated type and in various titers. If appropriate, one can also use entwisted and entwined threads. In the examples presented here, an entwisted optical monofilament fiber of PMMA with a diameter of 125 micrometers and a titer of 370 dtex (corresponding to 370 grams per 10'000 m thread length) was used. For the stitching of the optical fibers onto the flat support a stitch fixation thread of textured polyester with 113 dtex was used. A polyester woven fabric with a square meter weight of 80 grams/m² was used as support material.

The planar-like support structure can be made from various structures such as textiles or foils, and it is preferably flexible and suitable for draping. The optical fibers are attached onto the support by a stitching technique, which allows a considerable freedom of design in respect of how the light-emitting elements are arranged. Usually, stitching is carried out according to the two-thread method, in which the front thread is a light supplying thread and the back thread is a supporting thread. However, it is possible to use an inverted version of this principle or other combinations with two or more threads. The two thread systems are brought together on the support structure, and together they form the stitching pattern.

For production of a light-conducting textile by a stitching technique, a support structure is required at least at the beginning. However, in order to save weight and to achieve better drapability of the light-emitting textile structure, the supply structure can be removed after the stitching process, for example by dissolving it in an appropriate solvent such as water. In order to prevent the structure from disintegrating, the individual optical fibers need to be provided with appropriate connecting structures before the support is removed. Advantageously, these connecting structures are formed in the course of the stitching process.

Figure 8:
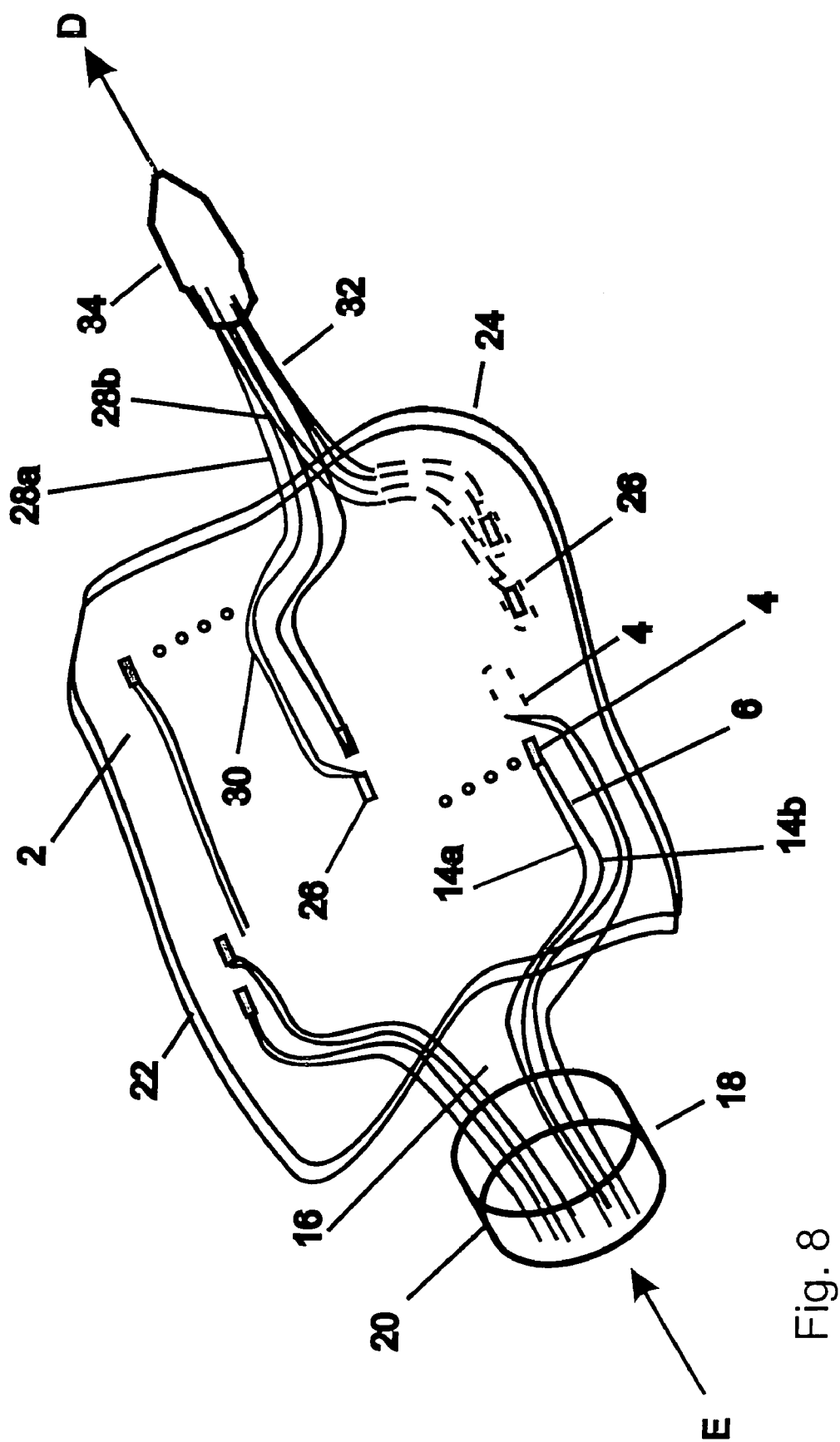
FIG. 8: a light-emitting textile structure useful for medical purposes, in a schematic drawing.

FIG. 8 represents a light-emitting textile structure that is useful for medical and veterinary applications. It comprises a flexible flat support 2 made of a textile material and a plurality of light-emitting elements 4 fixed thereto, only a small number of which is shown in the figure, however. Each light-emitting element is situated in the vertex region of a U-shaped optical fiber 6, so that each fiber 6 has a side pair 14*a*, 14*b*. The plurality of side pairs 14*a*, 14*b* is gathered near the ends thereof to a first fiber bundle 16, which is surrounded by a ring 18. In the example shown here, this is a metallic ring with a nominal width of 5 mm. The light input zone 20 thus formed is designed for coupling to a conventional incoherent light source, i.e. a lamp or a light-emitting diode (LED), or else to a coherent laser light source. Optionally, the fiber bundle may be formed as an optical cable over a certain length. The intensity distribution and the spectral distribution of the light that is coupled in along entrance direction E and, optionally, also its polarization are chosen according to the application of interest and can be adjusted by known techniques.

The textile structure shown in FIG. 8 further comprises a light reflection layer 22 that is attached to the back of support 2, which reflection layer allows one to achieve an increased light emission in the opposite front direction of the textile structure. In this sense, it is also possible to make the support itself from a light reflecting material, for example from a light reflecting foil. Furthermore, the light-emitting textile structure is provided at the front side thereof with a light scattering layer 24, by means of which a particularly homogeneous light emission distribution is achieved. The drawing of FIG. 8 visualizes the light scattering effect of layer 24 by means of a blurred appearance of the elements lying behind it.

As further seen from FIG. 8, the textile structure is provided with a number of light collectors 26, by means of which light impinging onto the textile structure can be detected In the example shown, the light collectors 26 are made up in the same way as the light-emitting elements 4, with the corresponding sides 28*a* and 28*b* of the optical fibers 30 being gathered to a second fiber bundle 32. The latter leads to a light output zone 34, from which the collected light is conducted, in detection direction D, to an optical detection device. The operating principle of this arrangement relies on an inversion of the principle of the light-emitting elements 4, i.e. the absence of total reflection at the output zones of the optical fibers not only allows an exit of light from the fiber, but also an entrance of light into the fiber. As an alternative to this embodiment, the textile structure may be provided with appropriate photoelectric light detectors.

By collecting the light impinging onto the textile structure, the characteristics of the light emitted from an irradiated tissue area can be investigated. This characteristic is determined both from the light that is directly reflected from the tissue, but also from the fluorescence radiation of the tissue; it may be possible to separate the corresponding fractions due to their different spectral distribution, optionally with the help of optical filters or other appropriate optical elements. Alternatively or in addition, the irradiation carried out with light of a first wavelength that is optimal for photodynamic therapy can be interrupted for a short time in order to collect the fluorescence intensity under irradiation with light of a second wavelength that is optimal for photodynamic diagnosis. Therefore, a determination—carried out continuously or from time to time—of the fluorescence intensity of an irradiated tissue area allows the investigation of progressive bleaching of a photosensitizer that was previously delivered or applied. Moreover, photodynamic diagnosis can be performed in situ.

For photodynamic therapy with 5-aminolevulinic acid, it is preferable to use a wavelength in the range of 635 nm whereas for photodynamic diagnosis with protoporphyrin IX a wavelength of approximately 400 nm is required.

While for most medical applications it is desirable for the light emission to be as homogeneous as possible, there are also application fields for which it is desired to have an inhomogeneous distribution of light emission. This can be achieved by virtue of the individual addressability of the various light-emitting elements. To this end, it would be necessary in case of the example of FIG. 8 to ensure that each one of the side pairs 14a, 14b is supplied with a predefined light intensity, for which one has to arrange for appropriate light input means.

Figure 9:
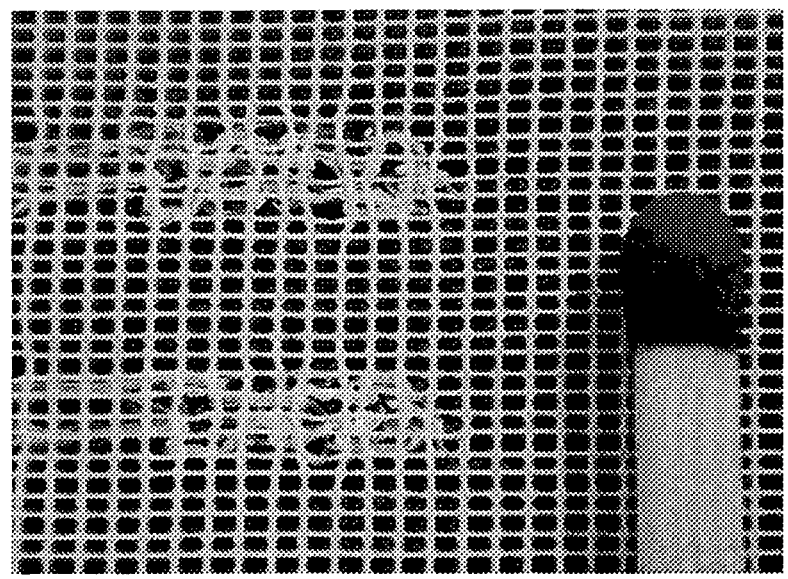
FIG. 9: two light-emitting elements fixed to a flat support, and a match for comparison of magnitude, as a photographic reproduction.

As can be recognized in FIG. 9 from a comparison of magnitude with a match, the individual light-emitting elements can be produced, for example, with a width of approximately 1 mm and a length of approximately 6 mm.

Figure 10:
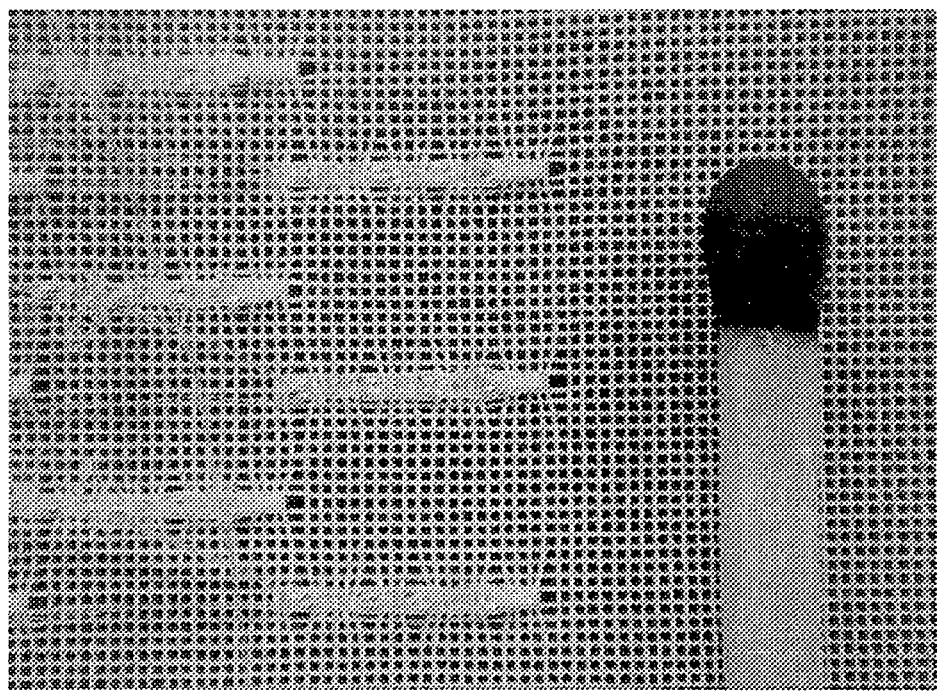
FIG. 10: several light-emitting elements fixed to a flat support, and a match for comparison of magnitude, as a photographic reproduction.

While the light-emitting elements shown in FIG. 9 comprise clearly developed loops, the light-emitting elements shown in FIG. 10 comprise loop less U-shaped end sections, each of which is fixed by a number of fixation stitches onto the flat support. It has been shown that with these light-emitting elements light emission mainly occurs in the neighborhood of the fixation stitches.

What is claimed is:

1. A light-emitting textile structure, in particular for medical purposes, comprising:
   a flat flexible support (2) and a plurality of light-emitting elements (4, 4a, 4b) affixed thereto: wherein each light-emitting element further comprises a light-supplying optical fiber (6, 6a, 6b), said optical fiber not being a woven or integral part of said flexible support, characterized in that to each optical fiber (6, 6a, 6b) there is associated exactly one light-emitting element (4, 4a, 4b) that comprises at least one output zone (8, 8a, 8b) formed by a local curvature (12,13) of the optical fiber by either a fixation stitch or at least one loop.

2. The textile structure according to claim 1, wherein said light-emitting elements form a pixel-like two dimensional arrangements (4(1,1), 4(1,2), 4(2,1), 4(2,2), 4(3,1,), 4(3,2)).

3. The textile structure according to claim 1, wherein said light-emitting elements (4, 4a, 4b) are stitched to the support (2), wherein said light-emitting elements are not a woven part of said support.

4. The textile structure according to claim 1, wherein each light-emitting element has two light-supplying optical fibers ends (6, 6a, 6b).

5. The textile structure according to claim 1, wherein said at least one output zone is formed by a plurality of loops (8,12) of the optical fiber.

6. The textile structure according to claim 1, which has been coated with a photosensitive substance or a precursor thereof.

7. The textile structure according to claim 1, wherein said at least one output zone is formed by a local damage or distortion (12) originating from a fixation stitch (10a).

8. The textile structure according to claim 1, wherein said support (2) is formed by a flexible flat material being either a textile material or a foil.

9. The textile structure according to claim 1, wherein said support (2) is removable before use.

10. The textile structure according to claim 1, further comprising a light-reflecting backside (22).

11. The textile structure according to claim 1, further comprising an optically effective layer (24) independent of said optical fibers at said textile structure's front side.

12. The textile structure according to claim 1, further including at least one output zone of an optical fiber used as a light collector (26) in order to lead away light impinging onto the textile structure through the optical fiber(30).

13. The textile structure according to claim 12, wherein at least one end of said optical fiber is connected to a light detector.

* * * * *